United States Patent [19]
Arndt et al.

[11] Patent Number: 4,760,169
[45] Date of Patent: Jul. 26, 1988

[54] PROCESS FOR THE PREPARATION OF HYDROXYMETHYLENEALKOXYACETIC ACID ESTERS

[75] Inventors: Michael Arndt; Fritz Maurer, both of Wuppertal, Fed. Rep. of Germany

[73] Assignee: Bayer Aktiengesellschaft, Leverkusen, Fed. Rep. of Germany

[21] Appl. No.: 36,059

[22] Filed: Apr. 9, 1987

Related U.S. Application Data

[63] Continuation of Ser. No. 795,685, Nov. 6, 1985.

[30] Foreign Application Priority Data

Nov. 13, 1984 [DE] Fed. Rep. of Germany ....... 3441369

[51] Int. Cl.$^4$ ............................................. C07C 69/73
[52] U.S. Cl. .................................................. 560/183
[58] Field of Search ......................................... 560/183

[56] References Cited

U.S. PATENT DOCUMENTS

2,208,355 7/1940 Beer et al. .......................... 560/183
2,394,255 2/1946 Northey ............................. 560/183

OTHER PUBLICATIONS

Houben–Weyl *Methoden der Organischen Chemie*, VII/1 (1954) Georg Thieme, Publ. Stuttgart, pp. 44–51.

*Primary Examiner*—Paul J. Killos
*Attorney, Agent, or Firm*—Sprung Horn Kramer & Woods

[57] ABSTRACT

A process for the preparation of an hydroxymethylene alkoxyacetic acid ester wherein a mixture of an alkoxyacetic acid ester and a formic acid ester are reacted in the presence of an alcoholic solution of an alkali metal alcoholate.

7 Claims, No Drawings

PROCESS FOR THE PREPARATION OF HYDROXYMETHYLENEALKOXYACETIC ACID ESTERS

This is a continuation of application Ser. No. 795,685, filed Nov. 6, 1985, now pending.

The invention relates to a new process for the preparation of hydroxymethylenealkoxyacetic acid esters and/or alkali metal salts thereof from a formic acid ester and an alkoxyacetic acid ester in the presence of an alcoholic solution of an alcoholate.

It is already known that hydroxymethylene compounds are obtained if formic acid esters and carboxylic acid esters are reacted in the presence of an inert diluent, such as, for example, diethylether, and in the presence of alcohol-free alkali metal alcoholates. The disadvantages in this process consist in the fact that when fairly large amounts of hydroxymethylene compounds are prepared, the viscosity of the reaction mixture increases to such an extent during the reaction that the stirrability and the removal of heat are substantially impaired thereby and the yields are unsatisfactory (see Houben-Weyl-Müller, Volume VII/1, pages 46–49, Thieme-Verlag Stuttgart).

It is also known that ester condensation reactions of this type give better results under a pressure of carbon monoxide. Disadvantages in this process are the involved technical and safety factors associated with carrying out the reaction, carbon monoxide being employed in this process under a pressure of 30 to 40 atmospheres (see Houben-Weyl-Müller, Volume VII/1, pages 46–49, Thieme-Verlag Stuttgart).

Furthermore, it is generally known that all partial reactions in ester condensation are equilibrium reactions and that a high yield is only ensured if the reaction is carried out in the presence of an alcohol-free alcoholate.

It has now been found that hydroxymethylenealkoxyacetic acid esters of the formula I

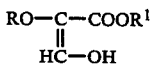

in which
R and $R^1$ are identical or different and represent alkyl having 1 to 4 carbon atoms,
and/or the alkali metal salts thereof,
are obtained if a mixture of an inert diluent and an alcoholic solution of alkali metal alcoholate is prepared, 60 to 80% by weight of the alcohol are removed from this mixture by distillation, and it is then reacted at a temperature of 0° C. to 40° C. with a mixture of an alkoxyacetic acid ester of the formula II

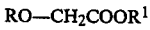   (II)

in which
R and $R^1$ have the meanings indicated above,
and a formic acid ester of the formula III

HCOOR$^2$   (III)

in which
$R^2$ represents $C_1$–$C_4$-alkyl.

By means of the process according to the invention it is possible, surprisingly, to carry out an ester condensation in very high yields in the presence of fairly cheap alcoholic solutions of an alcoholate. Further advantages of the process according to the invention consist in the fact that, as a result of using alcoholic solutions of an alcoholate, no substantial increase in the viscosity takes place, this ensures problem-free removal of the heat of reaction, and the use of pressure equipment involving safety complications is not necessary, instead of which it is possible to employ equipment which is customary in large-scale industrial plants.

It is preferable to use the process according to the invention to prepare compounds of the formula (I) in which R and $R^1$ are identical or different and represent alkyl having 1 to 4 carbon atoms.

It is particularly preferable to use the process according to the invention to prepare compounds of the formula (I) in which R and $R^1$ are identical or different and represent methyl, ethyl or n-propyl.

Suitable alkali metal salts of the compounds of the formula (I) are preferably, or particularly preferably, the sodium salts.

If methyl methoxyacetate, methyl formate and a methanolic solution of sodium methanolate are used as starting materials for the process according to the invention, the reaction can be outlined by means of the following equation:

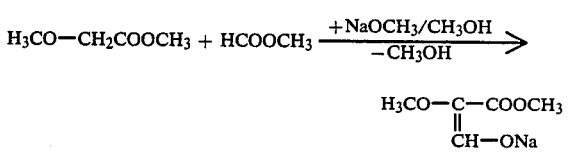

The alkoxyacetic esters required as starting materials for carrying out the process according to the invention are defined in general by the formula (II). In this formula, R and $R^1$ preferably have the meanings indicated above in the definition of the formula (I).

The following may be mentioned as examples of the compounds of the formula (II): methyl methoxyacetate, methyl ethoxyacetate, methyl n-propoxyacetate, ethyl methoxyacetate, ethyl ethoxyacetate, ethyl n-propoxyacetate, n-propyl methoxyacetate, n-propyl ethoxyacetate and n-propyl n-propoxyacetate.

The formic acid esters also to be used for the process according to the invention are defined in general by the formula (III). In this formula, $R^2$ preferably represents $C_1$–$C_2$-alkyl.

The following may be mentioned as examples of the compounds of the formula (III): methyl formate and ethyl formate.

The compounds of the formula (II) and (III) are compounds generally known in organic chemistry.

The process, according to the invention, for the preparation of the compounds of the formula (I) is carried out with the use of inert diluents. These include, in particular, aromatic hydrocarbons, such as benzene, xylene and toluene, and ethers, such as methyl tert.-butyl ether, diethyl ether and dibutyl ether. It is particularly preferable to employ xylene as the diluent.

The process according to the invention is carried out in the presence of an alcoholic solution of an alcoholate. Alkali metal alcoholates, such as sodium methylate and ethylate, have proved particularly suitable. Methanol is employed as the alcohol if sodium methylate is used, and ethanol is employed if sodium ethylate is used.

In general, the process according to the invention is carried out at temperatures between 0° C. and 40° C.

The preferred range is between 0° C. and 20° C. The reactions are carried out under normal pressure.

The process according to the invention is carried out by employing 1 to 3 moles, preferably 1.8 to 2.2 moles, of formic acid ester of the formula (III) and 1 to 2 moles, preferably 1.3 to 1.7 moles, of alkali metal alcoholate for 1 mole of the compound of the formula (II). Before distillation, the alcoholic solution of alkali metal alcoholate contains 3.5 to 5.5 moles, preferably 4 to 5 moles, of alcohol for 1 mole of alkali metal alcoholate, and, after the distillation, contains 0.6 to 2.2 moles, preferably 0.8 to 2.0 moles, of alcohol. The working up of the compounds of the formula (I) can be carried out by customary methods. The reaction product is preferably employed in the next reaction without further working up.

The compounds of the formula (I) and/or alkali metal salts thereof which can be prepared by the process according to the invention are important intermediates products for the preparation of known pest-combating agents (see, for example, DE-OS (German Published Specification) 2,928,185).

The further processing of the compounds of the formula (I) to give known pest-combating agents may be illustrated, for example, by means of the following scheme:

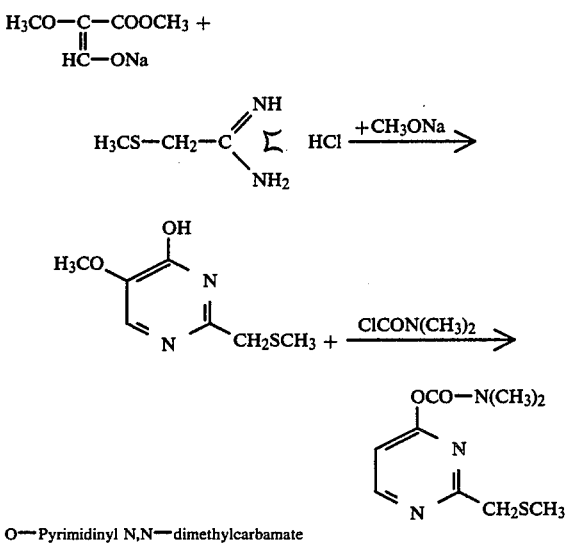

O—Pyrimidinyl N,N—dimethylcarbamate

PREPARATION EXAMPLE

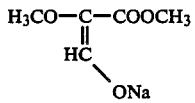

160 g of methanol are removed by distillation from a mixture of 315 g of 25% strength methanolic sodium methylate solution and 500 ml of xylene (technical mixture of isomers). 104 g of methyl methoxyacetate and 120 g of methyl formate are then added simultaneously at 5° C. to 10° C. The mixture is then stirred for a further hour at 20° C., the phases are separated and the phase containing the reaction product is employed in the subsequent reaction without further working up.

437 g of a 30% strength (85% of theory) solution of the sodium salt of methyl hydroxymethylenemethoxyacetate are obtained in this way.

COMPARISON EXAMPLE 1 mole of methyl methoxyacetate and 2 moles of methyl formate are initially placed in a pressure reactor, and 1 mole of solid sodium methylate is metered in at 0° to 10° C. The reactor is closed and stirred at 70° C. under a carbon monoxide pressure of 40 atmospheres until no further carbon monoxide is absorbed. When the reaction is complete, the product is filtered off, rinsed with methyl formate and dried.

131 g (85% of theory) of the sodium salt of methyl hydroxymethylenemethoxyacetate are obtained.

We claim:

1. Process for the preparation of an alkali metal salt of a hydroxymethylenealkoxyacetic acid ester of the formula (I)

$$\begin{array}{c} RO-C-COOR^1 \\ \| \\ H-C-OH \end{array} \quad (I)$$

in which

R and $R^1$ are identical or different and represent alkyl having 1 to 4 carbon atoms, and/or of alkali metal salts of the abovementioned esters, wherein a mixture of an inert diluent and an alcoholic solution of an alkali metal alcoholate containing 3.5 to 5.5 moles of alcohol is prepared, 60 to 80% by weight of alcohol is removed from this mixture by distillation, and the residue is then reacted at a temperature of 0° C. to 40° C. with a mixture of an alkoxyacetic ester of the formula $$RO-CH_2-COOR^1$$

in which

R and $R^1$ have the meaning indicated above, and a formic acid ester of the formula $$HCOOR^2$$

in which $R^2$ represents $C_1$-$C_4$-alkyl.

2. Process according to claim 1, wherein the inert diluent is an aromatic hydrocarbon or ether.

3. Process according to claim 2, wherein the inert diluent is benzene, xylene, toluene, methyl tert.-butyl ether, diethyl ether and dibutyl ether.

4. Process according to claim 1, wherein the alkali metal alcoholate is sodium methylate or sodium ethylate.

5. Process according to claim 1, wherein the alcohol is methanol or ethanol.

6. Process according to claim 1, wherein the reaction is carried out between 0° and 20° C.

7. Process according to claim 1, wherein 1 to 3 moles of formic acid ester and 1 to 2 moles of alkali metal alcoholates are employed per mole of the alkoxy acetic ester.

* * * * *